United States Patent [19]

Stoller et al.

[11] Patent Number: 4,557,273

[45] Date of Patent: Dec. 10, 1985

[54] METHOD AND APPARATUS FOR DETECTING OVULATION

[76] Inventors: Kenneth P. Stoller, 341 S. Bentley Ave., Los Angeles, Calif. 90049; Barry E. Taff, 8665 Pickford St., Los Angeles, Calif. 90035

[21] Appl. No.: 453,744

[22] Filed: Dec. 27, 1982

[51] Int. Cl.$^4$ ............................ A61B 5/04; A61B 5/10
[52] U.S. Cl. ..................................... 128/738; 128/639
[58] Field of Search ......................... 128/738, 639, 733

[56] References Cited

U.S. PATENT DOCUMENTS

| | | | |
|---|---|---|---|
| 3,924,609 | 12/1975 | Friedenberg et al. | 128/738 |
| 4,148,304 | 4/1979 | Mull | 128/738 X |
| 4,246,907 | 1/1981 | Bullock | 128/738 |
| 4,249,538 | 2/1981 | Musha et al. | 128/639 X |
| 4,261,371 | 4/1981 | Reading | 128/738 |
| 4,312,360 | 1/1982 | Conway et al. | 128/738 X |

*Primary Examiner*—Kyle L. Howell
*Assistant Examiner*—John C. Hanley
*Attorney, Agent, or Firm*—Philip D. Junkins

[57] ABSTRACT

A method and apparatus for the daily measurement of bioelectrical potentials of ovulating women in the area of their finger tips during their menstrual cycle to determine a midcycle peak potential as an indicator of the time of ovulation and thereby provide means for predicting the time for coitus for conception or for predicting the time for abstaining from coitus as an elective means of avoiding conception. Measurement of the finger-tip bioelectrical potential is accomplished through the use of a hand-held, non-invasive ovulation determinator which includes a D.C. potential scanning microgrid electrode applied to a finger tip for locating a site thereon of maximum D.C. potential in relation to the bioelectrical D.C. potential value of a ground electrode applied by the determinator to a hand surface area remote from the finger tip. Thereafter, the determinator measures the maximum bioelectrical D.C. potential value difference between such electrodes and reports the value difference, through appropriate electronic circuitry, in digital display fashion as a voltage value whereby over the 24-34 day term of the menstrual cycle a distinct rise in the voltage value indicates the time of ovulation.

10 Claims, 5 Drawing Figures

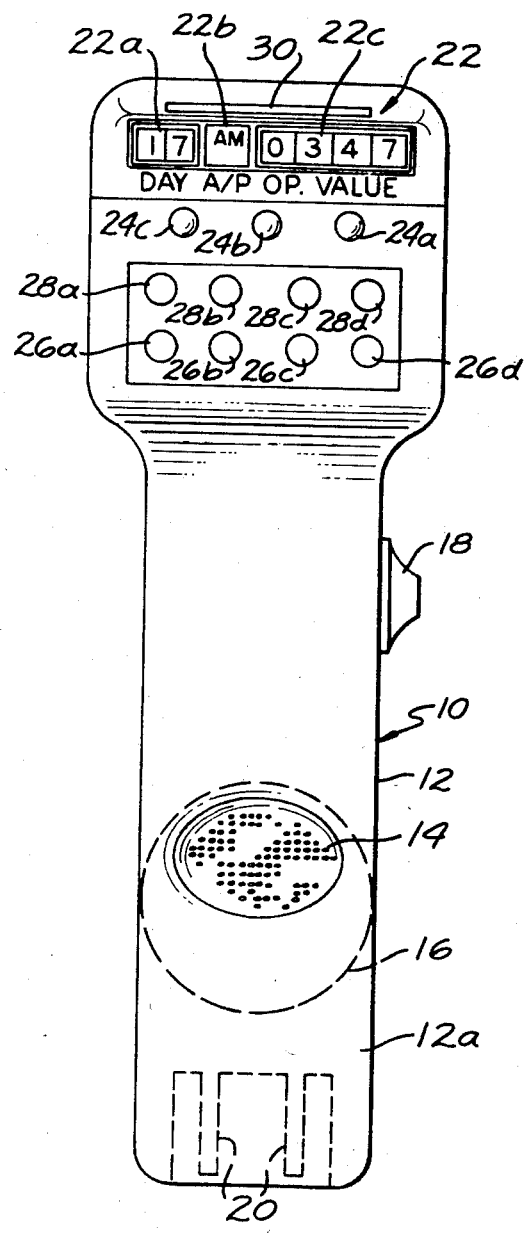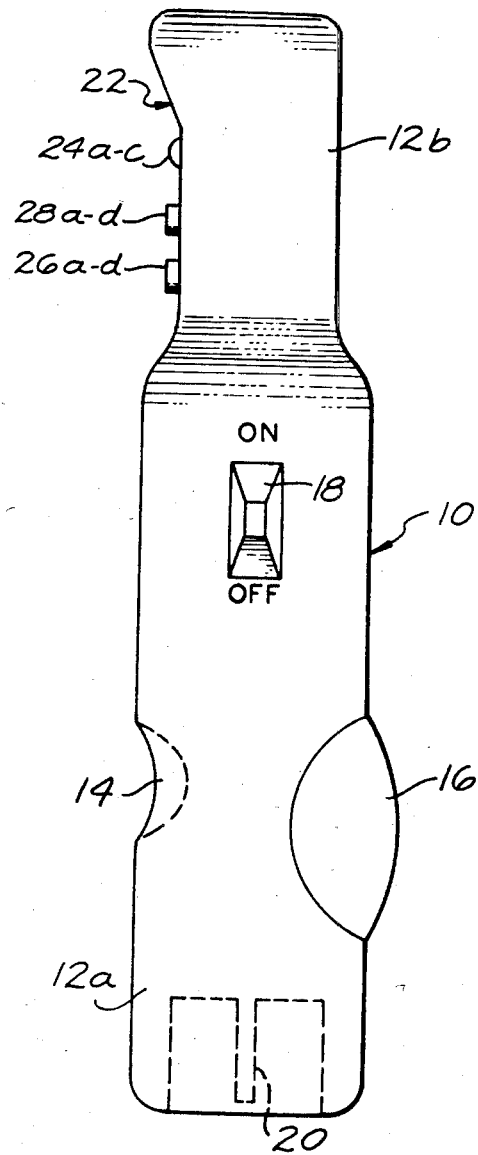
FIG. 1
FIG. 2

METHOD AND APPARATUS FOR DETECTING OVULATION

BACKGROUND OF THE INVENTION

This invention relates to a method and apparatus for measuring bioelectrical potentials at selected points on the body surface of ovulating women during their menstrual cycles to determine a midcycle peak potential as an indicator of the time of ovulation and thereby provide means for predicting the time for coitus for conception or for predicting the time for abstaining from coitus as an elective means of avoiding conception.

Over the past 20–30 years world attention has been drawn to the types of contraceptive devices and methods of contraception available to women and men. Some devices and methods are more effective than others but may have undesirable effects that make them more or less acceptable and to many individuals not acceptable at all. It is now clear that there is no single contraceptive device or method suitable to a majority of the couples engaging in coitus or contemplating such act. Many physicians have recommended, and many couples have found, that a natural method of family planning is an appealing choice. The appeal may stem from dissatisfaction with known contraceptive devices and means, personal reasons and beliefs (including religious condemnation) or from an interest in gaining better insight into one's own reproductive capabilities or cycles.

Today, natural family planning no longer depends on the "rhythm system," a much criticized and obsolete method of avoiding conception based upon the pattern of menstrual cycle regularity. Rather, the organized collection and graphing of data, such as a woman's basal body temperature, during the reproductive cycle is now used to indicate the fertile/infertile phases of the menstrual cycle. However, the basal body temperature (BBT) graph is monophasic in up to 20% of all ovulating women. Furthermore, a BBT graph is not useful in precisely identifying the time of ovulation because the shift in temperature can be out of synchrony with ovulation by as much as 3–6 days. The BBT graph also cannot be used to accurately predict the time for engaging in coitus for conception since it only indicates in retrospect when coitus should have occurred in order for conception to have taken place. Nevertheless, natural family planning utilizing BBT graphic predictions of ovulation has been shown to be 90% effective for couples spacing their children and 95% effective for those who have attained their desired family size (the difference is due to motivation). This is the same order of effectiveness as barrier contraception (diaphragm) and is considered acceptable for that method. Rather slow acceptance of natural family planning has resulted primarily because of lack of confidence in the BBT curves. Other methods of contraception (IUD's, oral contraceptives, etc.) are more effective but are intrusive of the body and may result in harmful side effects.

As previously stated, the present invention relates to a method and apparatus for determining the time of ovulation by measuring bioelectrical potentials at selected sites on the body surface of ovulating women during their menstrual cycle. Direct current potentials on the dermal (skin) surfaces of man and other vertebrates have long been described, measured and correlated with a variety of biological functions. Standing D.C. potential patterns over the human body were described by H. S. Burr and F. S. C. Northrup in their paper entitled "The Electrodynamic Theory of Life," *Quarterly Review of Biology*, 1955 10, 322–333. More recently the D.C. potential fields have been mapped with some precision and the pattern has been found to be roughly parallel to the gross anatomical arrangement of the central nervous system. R. O. Becker concluded that two bioelectric data transmission and control systems coexist in man and most other present-day vertebrates, i.e., one a sophisticated, action potential, digital-type system, and the other, a more basic primitive analog-type system, "The Basic Biological Data Transmission and Control System Influenced by Electrical Forces," *Annals New York Academy of Sciences*, 1974, 236–241. Becker further observed dermal D.C. voltage sources along the course of the peripheral data channels of the analog-type system and noted that such sources show lower resistance and higher voltage values.

An early study by H. S. Burr and L. K. Musselman on menstruation suggested the possibility of recording electrically, ovulation in the healthy human female, "Bio-electric Phenomena Associated with Menstruation," *Yale Journal of Biology and Medicine*, 1936, 9, 155–58. In 1937, Burr et al were able to document the bioelectric record of the "instant" of ovulation in a human female, "Bio-electric Correlates of Human Ovulation," *Yale Journal of Biology and Medicine*, 1937, 10, 154–160 and these investigators suggested that it may be possible to obtain bioelectric records of ovulation from points of contact with the body at other than the symphysis pubis and the vagina. Twenty years later, Parsons et al confirmed that vaginal-cervical electropotentials form characteristic cyclic patterns, with a midcycle peak of potential at the time of ovulation, and that midcycle potential change is not found in post-menopausal, irradiated or surgically castrated women, "Abdomino-Vaginal Electric Potential Differences with Special Reference to the Ovulating Phase of the Menstrual Cycle," *American Journal of Obstetrics and Gynecology*, 1958, 75, 121. They also showed that measured temperature, pH and psychogenic factors, while allied to potential differences, could not give the repetitive and cyclic electrical changes observed during the menstrual cycle in presumed association with periodic ovulation.

SUMMARY OF THE INVENTION

It has been discovered that by daily measurement of the bioelectrical potentials of ovulating women in the area of their finger-tips, throughout their menstrual cycle, a D.C. voltage value pattern is developed which includes a distinct peak voltage value at the time of ovulation. Measurement of the finger-tip bioelectrical potential, in accordance with the present invention, is accomplished through the use of a novel hand-held, non-invasive ovulation determinator. The ovulation determinator includes a D.C. potential scanning, microgrid electrode applied to a finger tip for locating a site thereon of maximum D.C. potential in relation to the bioelectrical D.C. potential value of a ground electrode applied by the determinator to a hand surface area remote from the finger tip. Thereafter, the determinator measures the maximum bioelectrical D.C. potential value difference between such electrodes and reports such D.C. potential value difference, through appropriate electronic circuitry, in digital display fashion as a voltage value. For the most part, throughout the menstrual cycle, measurements of D.C. potential value difference, via the present ovulation determinator, fall within a relatively narrow value range. Measurements of D.C. potential value difference, by the methodology of this invention, at the time of ovulation in the menstrual cycle show a dramatic increase in the value difference causing a distinct midcycle peak value in a curve of daily values plotted over the span of the menstrual cycle (normally 24–34 days). The distinct rise in the finger tip D.C. potential, at the time of ovulation, lasts for only 12 to 14 hours thereby dictating that, over the menstrual cycle, two measurements of D.C. potential should be made per day, i.e., once in the morning after rising and once in the evening at bedtime.

It is accordingly an object of this invention to provide a bioelectrical, D.C. potential-measuring method to be applied to selected dermal sites of ovulating women to obtain D.C. potential values relating to the fertile and infertile phases and peak fertility (midcycle) period of the menstrual cycle.

It is another object of the invention to provide a non-invasive, D.C. potential-measuring method to be applied to fingertip sites of ovulating women to obtain D.C. potential differential values, between such sites and a body ground site, which relate to the fertile and infertile phases and distinct peak fertility (midcycle) period of the menstrual cycle and which may be utilized to determine the time of ovulation in normally healthy women.

It is a further object of the invention to provide a non-invasive radiation-free D.C. potential-measuring device to be applied to finger-tip sites of ovulating women daily over the period of their menstrual cycle to obtain D.C. potential differential values, between such sites and a body ground site, which relate to the fertile and infertile phases and distinct peak fertility (midcycle) period of the menstrual cycle and which may be utilized to determine the time of ovulation in normally healthy women.

It is yet another objective of the invention to provide, in such a non-invasive device, means for scanning the finger-tip sites to which the device is applied to locate points thereon of maximum D.C. potential and means for reporting the D.C. potential value difference between such finger points and a body ground point in digital display fashion as a numerical voltage value.

BRIEF DESCRIPTION OF THE DRAWINGS

The foregoing and other objects, features and advantages of the invention will become apparent hereinafter from the following detailed description of the invention taken in conjunction with the accompanying drawings wherein:

FIG. 1 is a front view of the compact, portable electronic ovulation determinator of the present invention;

FIG. 2 is a side view of the ovulation determinator shown in FIG. 1;

DETAILED DESCRIPTION OF THE INVENTION

Figure 3:
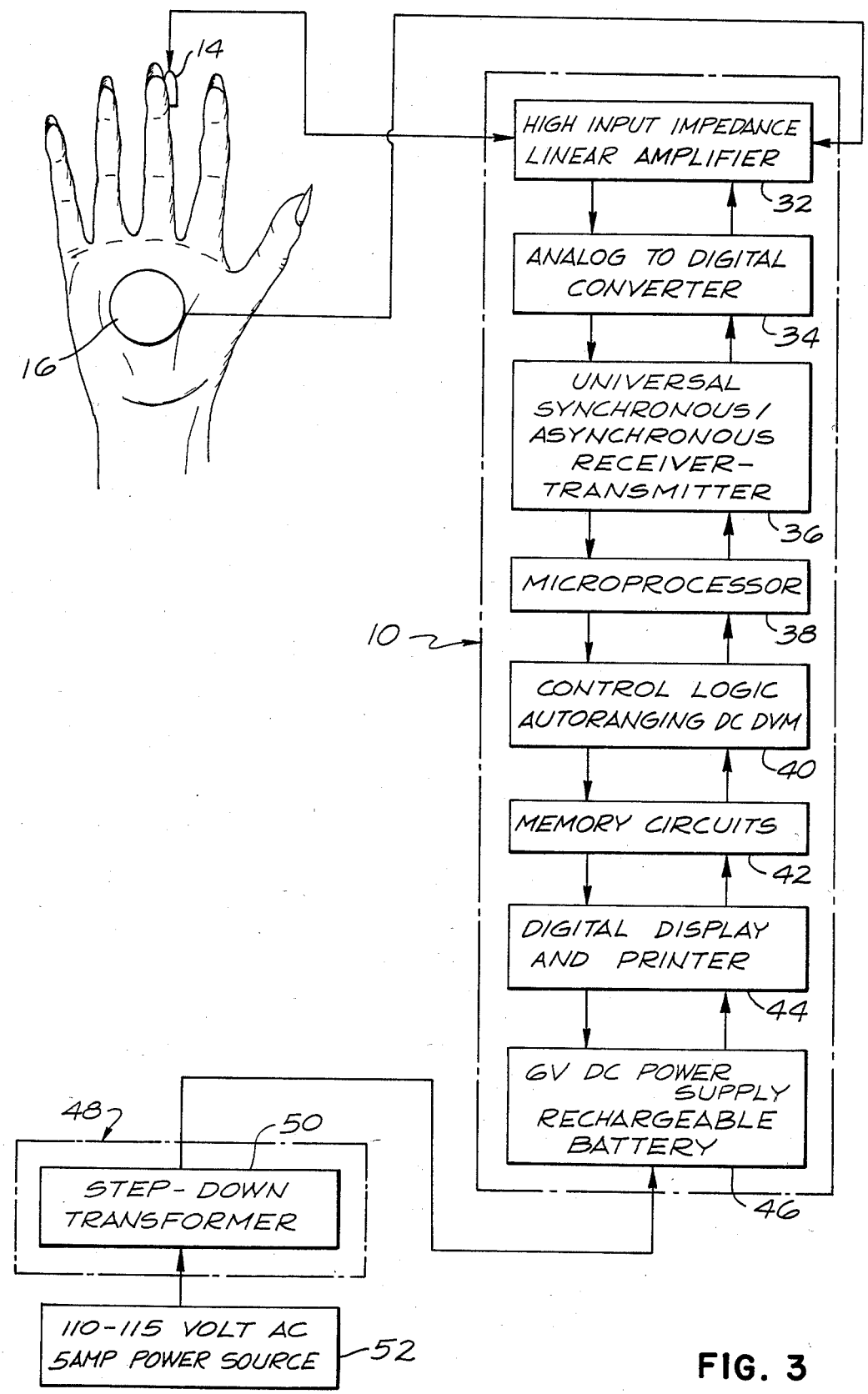
FIG. 3 is a basic block circuit diagram of the ovulation determinator according to the invention.

Referring now to the drawings, a preferred embodiment of the invention is illustrated in FIGS. 1 and 2 and comprises a bioelectrical measuring instrument module 10 adapted for measuring the D.C. potential differential values between finger-tip sites of ovulating women and a remote body ground site. The measuring instrument 10, referred to as an ovulation determinator, is comprised of an elongated casing 12 which encloses appropriate electronic circuitry, described hereinafter, and which bears on its handle portion 12a a finger-tip microgrid electrode 14 and a palm ground electrode 16. The casing handle portion 12a also bears an on-off switch 18 for energizing the electronic circuitry of the instrument and it is fitted internally with electrically conductive jack members 20 for connecting the instrument module, and its self-contained rechargeable battery, to a recharge module.

A head portion 12b of instrument casing 12 bears a digital display unit 22 of any suitable type which includes: section 22a for displaying a two digit day designation, section 22b for displaying an AM-PM time designation, and section 22c for displaying a four digit ovulation D.C. potential differential value in millivolts. The head portion 12b of casing 12 also bears a set of light emitting diode (LED) type indicators 24a, 24b and 24c which provide visual indication that: the instrument's circuitry is energized (LED 24a), the rechargeable battery within the instrument is adequately charged (LED 24b), and the finger microgrid electrode 14 and palm ground electrode 16 are in proper contact with a finger tip and palm of an individual holding the ovulation determinator (LED 24c). In addition, head portion 12b bears a bank of control buttons which direct the instrument in its ovulation potential value measuring, indicating and data storing functions, and memory recall and data print-out functions. Specifically, such control buttons include ovulation potential value measurement and entry control buttons 26a–d for: setting and displaying the day designation (26a), setting and displaying the AM-PM time designation (26b), measuring and displaying the ovulation D.C. potential differential value measurement (26c), and transferring the day, time and value displayed data to the memory circuits of the instrument for storage purposes (26d). The bank of control buttons also includes memory recall and memory clearance buttons (28a–d) for: seeking and displaying a day designation (28a), seeking and displaying an AM-PM time designation with the resultant display of the appropriate ovulation D.C. potential differential value measurement (28b), printing out all stored data (28c), and clearing the memory circuits of all stored data (28d). A strip print-out of all stored data may leave the ovulation determinator module 10 through slot 30.

During use of the ovulation determinator module 10, in accordance with the invention, the instrument is placed in the hand (right or left) of a woman subject for whom an ovulation D.C. potential differential value measurement is to be taken. With the palm of the hand positioned in a generally upwardly facing orientation the handle portion 12a of the determinator is placed across the palm with the palm ground electrode interfacing with the central portion of the palm. The subject grips the determinator placing the terminal phalanx of the forefinger, middle finger, or fourth finger into the concave-shaped finger microgrid electrode 14 positioned on the handle portion 12a of the determinator opposite the palm electrode 16. The concave shape of the finger electrode is such that the radial aspect of the terminal phalanx of the finger (for which a D.C. potential measurement is to be taken), just proximal to the nail bed, comes into full contact with the electrode 14. Although any one of the aforementioned fingers, in their terminal phalanx, can be utilized as the site for measuring electrical potentials, it has been found that the radial aspect of the terminal phalanx of the middle finger of either hand of an ovulating human subject usually comprises a site for electrical potential measurement yielding the greatest differential D.C. potential value with respect to a ground site.

The casing 12 of the ovulation determinator module 10 is preferably a structure molded of insulating plastic material of any of a number of high impact types. The palm ground electrode 16, mounted in the casing wall in the handle portion 12a of the instrument, may be fabricated of stainless steel or other highly-conductive, non-corrosive metal. The concave-shaped finger microgrid electrode 14 comprises a multiplicity of highly-conductive, separated wires (gold or silver) set in an insulating matrix material such as epoxy resin. The concave contact surface of the finger electrode is highly polished so as to present a microgrid of wire-end contact points with the finger surface interfacing with the electrode. The multi-wire finger electrode 14 is connected to appropriate electrical potential scanning circuitry within the instrument which locates the point site on the subject's finger which presents the highest D.C. potential value with respect to ground potential, such circuitry after locating the high value point site measures the differential D.C. potential value and report such value in digital display fashion.

A basic block circuit diagram of the ovulation determinator module 10, according to the invention, is illustrated in FIG. 3. The finger microgrid electrode 14 and palm ground electrode 16 of the determinator module are shown schematically to be in contact, respectively, with the radial aspect of the terminal phalanx of the middle finger of the hand of a subject and with the palm of the same hand of the subject. The finger electrode 14 and body ground electrode 16 are connected to the input terminals of a high input impedance linear amplifier 32 which converts the very low D.C. biopotentials sensed by such electrodes to low impedance higher voltage signals. An analog-to-digital converter 34 transforms the higher voltage outputs of amplifier 32 into a binary code of sensed voltages ranging between 0–999 millivolts. Binary encoded information respecting the biopotentials sensed by the finger and ground electrodes is received from the converter 34 by a universal synchronous/asynchronous receiver-transmitter 36. This receiver-transmitter polls and receives binary voltage data from all points being sensed by the finger-tip electrode (multiple points) and ground electrode (single point) in an ordered fashion and transmits such data to a micro-dataprocessor (computer) 38 which looks at the voltage data, forms such data into arrays, and picks the best available data for storage, manipulation and reporting purposes. Thus, the microprocessor picks the finger-tip site yielding the highest D.C. biopotential with respect to the sensed ground D.C. biopotential, subtracts the measured ground potential from the high value of finger-tip potential and develops a reportable differential, digital D.C. potential value.

The microprocessor 38 interfaces with an appropriate control logic autoranging D.C. digital voltmeter (DVM) 40 and memory circuitry 42 which in turn feed digital display and printer circuitry 44 whereby the high differential D.C. potential value, measured by the ovulation determinator, is reported in digital display fashion or printed out. The entire ovulation determinator circuitry package within casing 12 is energized by a rechargeable 6 volt D.C. battery 46, preferably of a common nickel-cadmium type, enclosed within the determinator module 10. The battery 46 is periodically recharged via recharge module 48 including a step-down transformer 50, fed by A.C. power source 52. The instrumentation apparatus of the invention is non-invasive of the subject's body and no electrical charge or stimulus is applied to the body by the device.

In carrying out the measurement of finger-tip biopotentials of ovulating women by the present method, the location and type of ground electrode is not critically important. It may in fact be placed in contact with other more remote portions of the body or may be held in the hand of the subject remote from the hand upon which a biopotential is being sensed by the finger electrode 14 of the determinator 10. Where the ground electrode is positioned or held at a body site more remote than the palm of the hand holding the determinator 10, the conductive cable leading to the ground electrode from the determinator should be provided with electrical shielding.

Pressure applied to the finger electrode 14 by the finger tip being sensed during the measurement of biopotential, may vary. Differences in such pressure may cause small quantitative changes in the reported and recorded potentials, but not qualitative changes from measurement time to measurement time over the extent of the menstrual cycle. However, it is desirable to apply relatively light finger-tip pressures to the finger electrode since this will minimize any skin or muscle reaction to such electrode. The subject should, therefore, be instructed to merely hold the determinator casing 12 in her hand as though holding a flashlight cylinder and curl the fingers lightly around the casing placing the tip of the middle finger (or other finger) lightly into contact with the concave-shaped finger electrode 14.

Use of the method and apparatus of the present invention for the daily measurement of bioelectrical potentials of ovulating women subjects in the area of their finger tips during their menstrual cycle to determine a midcycle peak potential, as an indicator of the time of ovulation, is further described in the following examples and the accompanying plot patterns of each subject's basal body temperature in comparison with finger-tip D.C. electrical potential measurements over the period of one or more menstrual cycles.

EXAMPLE 1

Using ovulation determination instrumentation substantially as described and illustrated herein, a healthy ovulating female subject (age 24), without any history of menstrual problems or irregularities, measured her finger-tip bioelectrical potentials over two 27-day menstrual cycles. The subject was instructed to take finger-tip potential measurements on the middle finger of each hand twice daily, once in the morning immediately after rising and once in the evening at bedtime. The subject was also instructed to be relaxed at the time of taking all finger-tip measurements, but not drowsy. All finger-tip electrical potential measurements were made by applying the finger electrode of the instrumentation to the same dermal site on the radial aspect of the terminal phalanx of the middle finger of each hand. During both cycles the subject's period of menses lasted approximately 7 days and bioelectrical potential measurements commenced on the 8th day and continued through the 27th day. Throughout the pre-ovulation, ovulation and post-ovulation periods of each menstrural cycle following menses (8th through 27th days) the subject measured her basal body temperature (BBT) each morning immediately after awakening.

Figure 4:
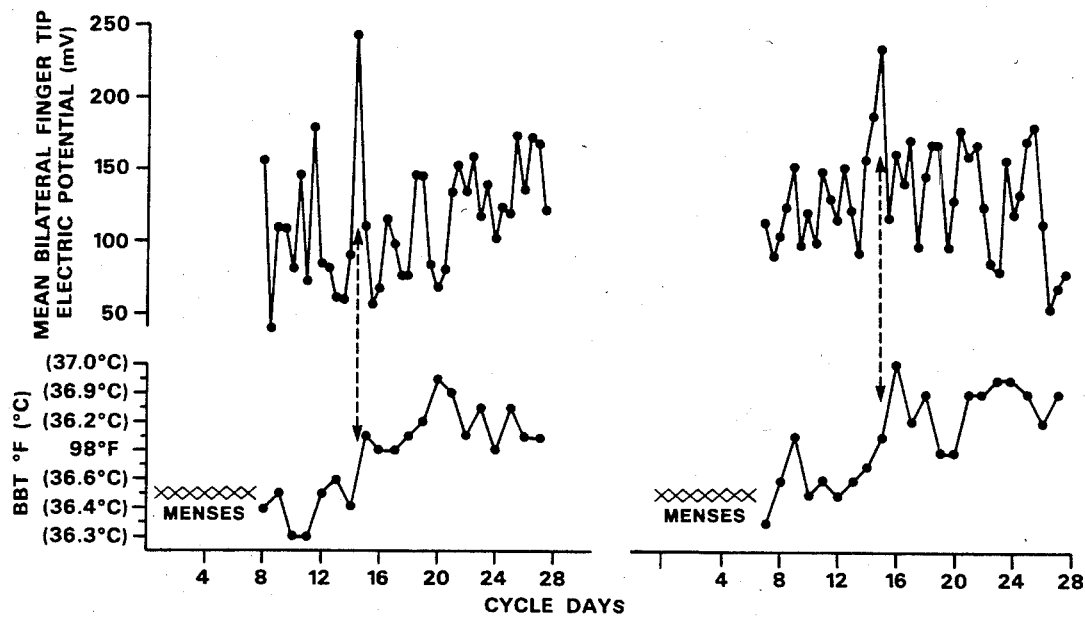
FIGS. 4 and 5 are drawings showing exemplary plot patterns of finger tip electrical potentials of healthy menstruating women measured twice daily by the ovulation determinator of the invention during menstrual cycles showing midcycle peak potential as an indicator of the time of ovulation.

FIG. 4 shows the plot patterns of the subject's BBT and finger-tip electrical potential measurements (the average of right-hand and left-hand potentials was used as the mean bilateral potential for each data point) for the two test menstrual cycles. Over the two cycles the mean bilateral potentials ranged between 40 and 250 millivolts and the difference between right-hand and left-hand potentials determining each mean bilateral potential value was less than 10 millivolts. The plots of mean bilateral electrical potentials show a distinct midcycle rise in D.C. potential during the 14th day of the first cycle and during the 15th day of the second cycle. These midcycle peaks in potential values correlate well with the classic BBT temperature shift which occurs the day after ovulation, i.e., the shift or rise in temperature is $\geq 0.5°$ F.

EXAMPLE 2

Using ovulation determination instrumentation substantially as described and illustrated herein, a healthy ovulating female subject (age 29), without any history of menstrual problems or irregularities, measured her finger-tip bioelectrical potentials over one 32 day menstrual cycle. The subject was instructed in the same manner as the subject in Example 1 with respect to the measurement of finger-tip potentials and basal body temperatures and measurements of finger-tip potentials was accomplished in the same fashion as Example 1. The subject's period of menses lasted approximately 5 days.

Figure 5:
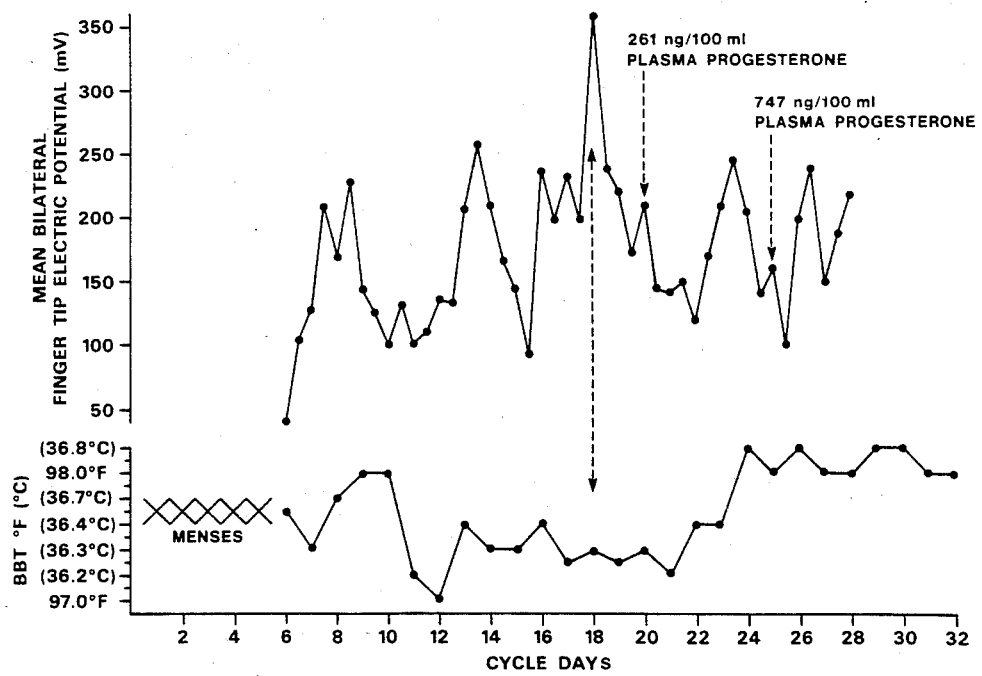

FIG. 5 shows the plot pattern of the subject's BBT and finger-tip electrical potential measurements (mean bilateral potential for each data point) for the test menstrual cycle. Over the cycle the mean bilateral potentials ranged between 40 and 350 millivolts and the difference between right-hand and left-hand potentials determining each mean bilateral potential value was less than 10 millivolts. The single-cycle plot of mean bilateral electrical potentials shows a distinct midcycle rise in D.C. potential during the 18th day of the cycle. The midcycle peak in mean potential value did not correlate well with the BBT shift which occurred approximately 6 days after the midcycle mean potential peak. Plasma progesterone was measured at two and seven days past the midcycle peak in mean potential in order to determine whether the distinct mean potential peak (18th day) reflected the beginning of the subject's luteal phase. That is, plasma progesterone was measured to determine whether the mid-cycle peak signified that ovulation had taken place on day 18. The measured two and seven day values of plasma progesterone were 261 ng/100 ml and 747 ng/100 ml, respectively, and correspond with luteal phase values that would be predicted two and seven days post-ovulation according to J. M. Shane et al., "The Infertile Couple," *Clinical Symposia* 28:5, 1976. The progesterone values and D.C. potential measurements both confirm that ovulation took place during the 18th day of the subject's menstrual cycle.

From the foregoing examples, it will be obvious that the present method and apparatus for measuring finger-tip bioelectrical potentials of ovulating women during their menstrual cycle to determine a midcycle peak potential as an indicator of the time of ovulation and thereby for predicting the time for coitus for conception or for predicting the time for abstaining from coitus as an elective means of avoiding conception, constitutes a superior means of making such predictions with respect to basal body temperature as an indicator of the time of ovulation. Finger-tip D.C. potentials are highly responsive to ovulation whereas basal body temperature may, in fact, indicate thermogenic non-responsiveness in pinpointing the time of ovulation and the shift of BBTs may be out of synchrony with ovulation for as much as 3-6 days. Furthermore, changes in sleep patterns and various psychogenic factors often invalidate BBTs. Conversely, as long as the D.C. dermal finger-tip potential is not determined during an acute period of emotional excitement or physical stress, sleep patterns and psychogenic factors seem to play an insignificant role in interfering with the D.C. potential results when measurements are taken by the subject in a generally relaxed state.

While this invention has been described in connection with a particular structural embodiment of an ovulation determinator, many modifications of the determinator apparatus and method of determining the time of ovulation in female human subjects will be apparent to those skilled in the art. Accordingly, such modifications are to be included within the spirit and scope of the invention as defined by the following claims.

We claim:

1. Apparatus for periodically measuring and reporting D.C. bioelectrical potentials of ovulating women subjects in the area of their finger tips during their menstrual cycle to determine a midcycle peak potential value as an indicator of the time of ovulation comprising:
   (a) a microgrid finger electrode including a multiplicity of separated wires adapted for multi-point D.C. bioelectrical potential sensing contact with the terminal phalanx portion of a finger on the hand of an ovulating woman subject;
   (b) a single wire ground electrode adapted for D.C. bioelectrical potential sensing contact with the body of said subject at a site remote from the contact site of the microgrid finger electrode;
   (c) means for receiving the multi-point D.C. bioelectrical potentials sensed by said microgrid electrode and the D.C. bioelectrical potential sensed by said single wire electrode and converting said D.C. potentials to low impedance higher voltage signals, said D.C. bioelectrical potential receiving and converting means including a high input impedance linear amplifier having input terminals in electrical communication with the multiplicity of wires of said microgrid finger electrode and the single wire ground electrode;
   (d) means for converting said higher voltage signals into a binary code of sensed digital voltage values, said signal converting means including an analog-to-digital converter having input terminals in electrical communication with said high input impedance linear amplifier;

(e) means for receiving coded binary digital voltage values from said analog-to-digital converter, polling said voltage values and placing said voltage values in ordered format, said voltage value receiving means including a universal synchronous/asynchronous receiver-transmitter having input terminals in electrical communication with said analog-to-digital converter;

(f) micro-dataprocessor means in electrical communication with said receiver-transmitter for receiving ordered digital voltage values from said receiver-transmitter, selecting the highest voltage value sensed by the microgrid finger electrode with respect to the voltage value sensed by the ground electrode, and developing a reportable differential, digital D.C. voltage value between said highest voltage value sensed by said microgrid finger electrode and said ground voltage value; and (g) means for displaying said differential voltage value in digital form as a numerical value of the D.C. bioelectrical potential of said woman subject at the time of measurement, the highest numerical value of D.C. bioelectrical potential measured over the menstrual cycle comprising a mid-cycle peak potential as indication of the time of ovulation of said subject.

2. Apparatus for measuring and reporting D.C. bioelectrical potentials of ovulating women subjects as defined in claim 1 wherein the finger electrode is concave-shaped to receive the subject's finger so that the radial aspect of the terminal phalanx of said finger, just proximal to the nail bed, comes into full and intimate contact with said electrode.

3. Apparatus for measuring and reporting D.C. bioelectrical potentials of ovulating women subjects as defined in claim 1 wherein the ground electrode is convex-shaped and is positioned with respect to the finger electrode for contact with the body of the subject in the palm area of the hand of the subject which presents a finger for contact with the finger electrode.

4. Apparatus for measuring and reporting D.C. bioelectric potentials of ovulating women subjects as defined in claim 1 wherein memory circuit means is electrically interconnected with said micro-dataprocessor for receiving and storing reportable differential, digital D.C. voltage values and for transmitting said stored values, upon recall, to said display means as a sequence of numerical values of the bioelectrical potential of said subject over the time frame of a menstrual cycle.

5. A method for periodically measuring and reporting D.C. bioelectrical potentials of ovulating woman subjects in the area of their finger tips during their menstrual cycle to determine a midcycle peak potential as an indicator of the time of ovulation comprising the steps of:

(a) establishing electrical contact between the dermal surface of the terminal phalanx portion of a finger on the hand of an ovulating woman subject and a multi-point electrical potential sensing microgrid finger electrode including a multiplicity of separated wires for sensing a multiplicity of D.C. bioelectrical potentials on said dermal surface of said finger;

(b) establishing electrical contact between the body of said subject and an electrical potential sensing single wire ground electrode at a site on the body remote from said microgrid finger electrode for sensing the D.C. bioelectrical potential at said remote body site;

(c) amplifying the multiplicity of D.C. bioelectrical potentials sensed by said microgrid finger electrode and the D.C. bioelectrical potential sensed by said ground electrode through a high input impedance linear amplifier to produce low impedance higher voltage signals corresponding to said multiplicity of D.C. potentials sensed by said finger electrode and said D.C. potential sensed by said ground electrode;

(d) converting said higher voltage signals into a binary code of sensed digital voltage values through an analog-to-digital converter;

(e) polling said sensed voltage values and placing said values in ordered format through a universal synchronous/asynchronous receiver-transmitter;

(f) processing said ordered digital voltage values through a micro-dataprocessor to select the highest voltage value sensed by the microgrid finger electrode with respect to the voltage value sensed by the ground electrode and developing through said micro-dataprocessor a reportable differential, digital D.C. voltage value between said highest voltage value sensed by said microgrid finger electrode and said ground voltage value; and (g) displaying said differential voltage value in digital form as a numerical value of the D.C. bioelectrical potential of said woman subject at the time of measurement, the highest numerical value of differential D.C. bioelectrical potential measured over the menstrual cycle comprising a midcycle peak potential as indication of the time of ovulation of said subject.

6. A method for measuring and reporting D.C. bioelectrical potentials of ovulating women subjects as defined in claim 5 wherein the electrical contact established between the finger electrode and a finger on the hand of an ovulating woman subject is made on the dermal surface of the radial aspect of the terminal phalanx portion of said finger proximal to the nail bed thereof.

7. A method for measuring and reporting D.C. bioelectrical potentials of ovulating women subjects as defined in claim 10 wherein the electrical contact established between the finger electrode and a finger on the hand of an ovulating woman subject is made on the dermal surface of the radial aspect of the terminal phalanx of the forefinger, middle finger, or fourth finger of said hand proximal to the nail thereof.

8. A method for measuring and reporting D.C. bioelectrical potentials of ovulating women subjects as defined in claim 5 wherein the electrical contact established between the ground electrode and a site on the body of the subject remote from said finger electrode is made on the hand of the subject which presents a finger for contact with said finger electrode.

9. A method for measuring and reporting D.C. bioelectrical potentials of ovulating women subjects as defined in claim 5 wherein the electrical contact established between the ground electrode and a site on the body of the subject remote from said finger electrode is made on the palm of the hand of the subject which presents a finger for contact with said finger electrode.

10. A method for measuring and reporting D.C. bioelectrical potentials of ovulating women subjects as defined in claim 11 wherein the differential voltage value displayed in digital form is stored in memory circuitry for subsequent recall comparison with other stored differential voltage values over the time frame of a menstrual cycle.

* * * * *